United States Patent [19]

Evans et al.

[11] Patent Number: 5,194,460

[45] Date of Patent: Mar. 16, 1993

[54] STORAGE STABLE HEAT CURABLE ORGANOSILOXANE COMPOSITIONS CONTAINING A MICROENCAPSULATED CATALYST AND METHOD FOR PREPARING SAID CATALYST

[75] Inventors: Steven M. Evans, Saginaw; Chi-Long Lee; Ming-Hsiung Yeh, both of Midland, all of Mich.

[73] Assignee: Dow Corning Corporation, Midland, Mich.

[21] Appl. No.: 815,780

[22] Filed: Jan. 2, 1992

[51] Int. Cl.$^5$ .................................................. C08K 9/10
[52] U.S. Cl. .................................. 523/211; 528/15; 525/478; 525/936
[58] Field of Search ............... 528/15; 525/478, 936; 523/211

[56] References Cited

U.S. PATENT DOCUMENTS

| | | | |
|---|---|---|---|
| 4,461,854 | 7/1984 | Smith | 523/211 |
| 4,481,341 | 11/1984 | Schlak et al. | 525/478 |
| 4,528,354 | 7/1985 | McDougal | 528/33 |
| 4,604,444 | 8/1986 | Donnadieu et al. | 528/34 |
| 4,766,176 | 8/1988 | Lee et al. | 525/100 |
| 4,784,879 | 11/1988 | Lee et al. | 427/213.34 |
| 4,874,667 | 10/1988 | Lee et al. | 428/402.22 |
| 5,009,957 | 4/1991 | Lee et al. | 528/15 |
| 5,015,691 | 5/1991 | Lewis et al. | 525/478 |
| 5,015,716 | :/1991 | Togashi et al. | 528/15 |
| 5,066,699 | 11/1991 | Lee et al. | 524/379 |
| 5,118,772 | 6/1992 | Herzig et al. | 528/15 |
| 5,135,960 | 8/1992 | Higuchi et al. | 528/15 |
| 5,136,065 | 8/1992 | Yeh | 556/415 |

FOREIGN PATENT DOCUMENTS 49-134786 12/1974 Japan .

*Primary Examiner*—John C. Bleutge
*Assistant Examiner*—Karen A. Dean
*Attorney, Agent, or Firm*—Robert Spector

[57] ABSTRACT

The present invention provides microencapsulated hydrosilylation catalysts for one-part heat curable organosiloxane compositions. Compositions containing these exhibit long-term storage stability yet cure rapidly when heated above the melting point of the encapsulating polymer. At least a portion of these microcapsules are less than one micron in diameter, and substantially all are less than about three microns in diameter. Compositions containing the preferred platinum group metals as catalysts are optically transparent.

The microencapsulated curing catalysts of this invention are prepared by irradiating with UV light in the wavelength range of from 300 to 400 nanometers a solution containing (1) at least one of a specified group of photocrosslinkable organosiloxane compounds derived from propargyl esters of carboxylic acids containing a terminal aromatic hydrocarbon radical and at least two ethylenically unsaturated carbon atoms and (2) a liquid or solubilized hydrosilylation catalyst.

6 Claims, No Drawings

STORAGE STABLE HEAT CURABLE ORGANOSILOXANE COMPOSITIONS CONTAINING A MICROENCAPSULATED CATALYST AND METHOD FOR PREPARING SAID CATALYST

BACKGROUND OF THE INVENTION

1. Field of the Invention

This invention relates to curable organosiloxane compositions. More particularly, this invention relates to one-part organosiloxane compositions that cure by means of a hydrosilylation reaction and contain a novel microencapsulated curing catalyst. The compositions exhibit long term storage stability under ambient conditions yet cure rapidly at elevated temperatures.

2. Description of the Prior Art

Organosiloxane compositions cure by a variety of reactions. Some of the more common curing means involve 1) a free radical reaction initiated by the heat-induced decomposition of an organic peroxide or the decomposition of a photoinitiator in the presence of ultraviolet light and 2) the reaction between a hydroxyl-containing polyorganosiloxane and an organosilicon compound containing two or more hydrolyzable groups that occurs under ambient conditions in the presence of moisture and a suitable catalyst.

One of the more useful classes of polyorganosiloxane compositions cures by a reaction between silicon-bonded hydrogen atoms and either silicon bonded alkenyl radicals or hydroxyl groups. These reactions are catalyzed by metals from the platinum group of the periodic table or compounds of these metals. The advantages of these compositions include their rapid curing rate, particularly at elevated temperatures, the absence of objectionable by-products produced during the curing of compositions containing organic peroxides or silanes with hydrolyzable groups such as acetoxy or methoxy, and the difficulty of achieving complete curing of moisture-curable organosiloxane compositions applied in thick layers.

Compositions that cure by a hydrosilylation reaction typically contain a polydiorganosiloxane with at least two ethylenically unsaturated hydrocarbon radical per molecule, an organohydrogensiloxane containing at least two silicon bonded hydrogen atoms per molecule in an amount sufficient to achieve curing of the composition and a platinum- or rhodium-containing catalyst in an amount sufficient to promote curing of the composition. Fillers and other additives may be present for the purpose of modifying physical and/or chemical properties of the composition either prior to or following curing.

Because organosiloxane compositions that cure by a platinum-catalyzed hydrosilylation reaction begin to cure even at ambient temperature once the reactants are combined, the catalyst and the organohydrogensiloxane reactant are usually packaged in separate containers and are not combined until it is desired to cure the composition. Even if the composition contains one or more of the known platinum catalyst inhibitors it cannot be stored in a single container for more than a few hours.

One of the alternatives proposed in the prior art to supplying platinum-catalyzed curable organosiloxane compositions as two-package materials is to isolate either the catalyst or the organohydrogensiloxane within a matrix of a material that is solid under the conditions encountered during storage of the curable composition, yet allows the entrapped reactant or catalyst to escape and mix with the other ingredients when it is desired to cure the composition.

The prior art discloses a number of different one-part curable organosiloxane compositions containing microencapsulated reactants or catalysts. An example of this type of composition is described in U.S. Pat. No. 4,528,354, which issued to McDougal and Dougherty on Jul. 9, 1985. This patent describes one-part peroxide curable silicone rubber compositions. The compositions include a microencapsulated liquid phase containing an organic peroxide in a shell of a resinous thermosetting material that is impervious to the peroxide.

The capsules are designed to rupture under a given internal vapor pressure that is generated by the encapsulated liquid when the curable composition containing the microcapsules is heated.

Because release of the peroxide is dependent upon rupturing rather than melting of the shell separating the peroxide from the other ingredients of the organosiloxane composition, the composition and thickness of the shell must be carefully controlled to ensure that the rupture of the capsules will occur reproducibly within the temperature range used to cure the organosiloxane composition.

U.S. Pat. No. 4,604,444, which issued to Donnadieu on Aug. 5, 1986 describes storage stable polyorganosiloxane compositions comprising a polyhydroxylated polyorganosiloxane, a polyfunctional acyloxysilane and a microencapsulated accelerator that either contains or generates water. The encapsulated material can be released using heat and/or irradiation. Suitable encapsulating materials include polystyrene, acrylonitrile-styrene copolymers, and poly(methyl methacrylate). This patent does not suggest using microencapsulated materials in organosiloxane compositions curable by means other than the reaction of polyhydroxylated polyorganosiloxanes with acyloxysilanes.

U.S. Pat. No. 4,461,854, which issued to Smith on Jul. 2, 1984 teaches two-part curable organosiloxane compositions. One part contains a silanol-terminated polyorganosiloxane and the second component contains a curing agent, a filler and an encapsulated catalyst. The catalyst is a specified group of metal salts of carboxylic acids where the metal is, for example, tin, lead or zirconium. The encapsulating material is preferably a salt of a carboxylic acid that does not promote room temperature curing of the composition. The encapsulated catalyst prolongs the bath life of the curable composition.

U.S. Pat. No. 4,481,341, which issued to Schlak et al. on Nov. 6, 1984 and Japanese published application No. 49/134,786, published on Dec. 25, 1974 describe thermosetting organosiloxane compositions comprising a polyorganosiloxane containing at least two ethylenically unsaturated hydrocarbon radicals per molecule, a polyorganohydrogensiloxane containing at least two silicon bonded hydrogen atoms per molecule and a platinum-containing catalyst that is dispersed in a finely divided, solid matrix, such as a silicone resin or an organic resin. The concentration of catalyst is from 0.001 to 5 percent by weight of platinum metal.

The finely divided material in which the catalyst is dispersed is virtually insoluble in either the aforementioned polyorganosiloxane or polyorganohydrogensiloxane and melts or softens at a temperature between 70 and 250 degrees C. The alleged advantage of the compositions disclosed in the patent to Schlak et al. is that the catalyst remains isolated from the other ingredients of the curable composition until the composition is heated sufficiently to melt the material in which the catalyst is dispersed. Because the organosilicon compounds present in the composition will not cure in the absence of the catalyst, the composition can allegedly be stored for long periods of time without undergoing curing or even an increase in viscosity.

A disadvantage of the curable organosiloxane compositions described by Schlak et al. and the published Japanese patent application is the method taught to prepare the catalyst/resin composition. A solid block or sheet of resin containing the platinum composition dispersed throughout is ground to a fine powder. Based on the random nature of the grinding operation there is a reasonable probability that some of the particles will contain platinum catalyst on their surface. Even trace amount of platinum have been shown to cause premature curing of the type of organosiloxane composition exemplified in this patent.

One way to avoid the inherent disadvantages of the catalyst compositions described in the Schlak et al. patent, is to completely microencapsulate finely divided particles or droplets of a catalyst composition within a material that is impermeable to the catalyst and effectively isolates it from the reactive ingredients of a curable organosiloxane composition. The encapsulant melts or softens at the desired curing temperature of the composition. A variety of methods for microencapsulating materials are known in the art.

U.S. Pat. No. 4,874,667, which issued on Oct. 17, 1989 to Lee et al. and is assigned to the same party as the present application discloses one-part organosiloxane compositions that cure by a platinum-catalyzed hydrosilylation reaction. The platinum catalyst is microencapsulated in one or two layers of a thermoplastic organic polymer. The diameter of the microencapsulated catalyst particles are less then 100 microns.

A disadvantage of the preparative methods described in the Lee et al. patent and related U.S. Pat. No. 4,766,176, issued on Aug. 23, 1988 and U.S. Pat. No. 4,784,879. issued on Nov. 15, 1988, is the inability of these methods to yield microcapsules of sufficiently small size that curable compositions containing these microcapsules are optically transparent. Curable compositions containing these microcapsules are translucent or opaque.

U.S. Pat. No. 5,066,699, which issued on Nov. 19, 1991 describes a method for preparing a microencapsulated platinum-containing hydrosilylation catalyst. A solubilized hydroxyl-containing ethylenically unsaturated organic compound is photopolymerized in the presence of the catalyst, a photoinitiator for the polymerization and an optional surfactant. Substantially none of the microcapsules is larger than 3 micrometers in diameter. This patent also discloses storage stable one-part curable organosiloxane compositions containing a microencapsulated catalyst prepared as described in the patent. The compositions are cured by heating them at a temperature that is at least equal to the softening temperature of the polymer portion of the microencapsulated catalyst.

One objective of this invention is to provide a novel type of microencapsulated platinum group metal-containing curing catalyst that does not detract from the optical transparency or the cure rate at elevated temperatures of curable organosiloxane compositions containing the catalyst.

A second objective is to provide a novel method for preparing microencapsulated hydrosilylation reaction catalysts that are effective curing catalysts for organosiloxane compositions.

Another objective is to provide optically transparent one-part storage stable organosiloxane compositions containing the microencapsulated curing catalysts of this invention. The compositions can be cured either by heating them or exposing them to ultraviolet radiation in the range of from 200 to 260 nanometers (nm).

SUMMARY OF THE INVENTION

The present invention provides microencapsulated hydrosilylation catalysts for one-part organosiloxane compositions that cure by a hydrosilylation reaction. In addition to exhibiting long-term storage stability compositions containing the preferred platinum group metal catalysts are optically transparent in the absence of opacifying additives. At least a portion of these microcapsules are less than one micron in diameter, and substantially all are less than about three microns in diameter.

The microencapsulated curing catalyst ingredient of the present curable compositions is prepared by the photoinitiated crosslinking of organosilicon derivatives prepared by a hydrosilylation reaction between an organohydrogensiloxane and a propargyl ester wherein the carboxylic acid portion contains a sequence of at least two conjugated ethylenic double bonds between the carbopropynoxy group and a terminal aryl or alkaryl radical.

DETAILED DESCRIPTION OF THE INVENTION

This invention provides a microencapsulated catalyst composition comprising a liquid or solubilized hydrosilylation catalyst encapsulated within at least one layer of at least one organosiloxane compound, where said organosiloxane compound is the cross-linked product obtained by exposing an organosiloxane compound containing repeating units of the formula $$QR^1_aSiO_{(3-a)/2}$$

to ultraviolet light of a wavelength from 300 to 400 nm, where Q represents the radical $$R^2(CH=CH)_n\text{—}CH=CH\text{—}CH=CR^3\text{-}C(O)OCH_2CH=CH\text{—}, \qquad (1)$$

each $R^1$ is individually selected from the group consisting of unsubstituted and substituted monovalent hydrocarbon radicals, $R^2$ represents an aryl, alkoxyaryl or alkaryl radical, $R^3$ is —C≡N or —C(O)OR$^4$, where $R^4$ represent an unsubstituted monovalent hydrocarbon radical, a is 0, 1 or 2 and n is 0 or a positive integer, with the proviso that n is 0 only when $R^2$ is naphthyl.

Unsubstituted hydrocarbon radicals that can be represented by $R^1$ and $R^4$ include but are not limited to alkyl radicals containing from 1 to 10 carbon atoms, such as methyl, ethyl and propyl, cycloalkyl radicals such as cyclohexyl, aryl such as phenyl, alkaryl such as tolyl and xylyl and aralkyl such as benzyl. Substituents that can be present on $R^1$ include but are not limited to halogens such a chlorine, bromine and fluorine. Most preferably $R^1$ and $R^4$ are methyl or phenyl and $R^1$ is 3,3,3-trifluoropropyl. The preferences for $R^1$ are based on the availability of the corresponding chlorosilanes used to prepare the organohydrogensiloxanes used to prepare the present organosiloxane compounds.

Preferred hydrosilylation catalysts are compounds of metals from the platinum group of the periodic table.

This invention also provides a one-part, storage stable, heat curable organosiloxane composition comprising A. a liquid or gum polyorganosiloxane containing an average of at least two ethylenically unsaturated hydrocarbon radicals per molecule;

B. as a curing agent for said composition, an organohydrogensiloxane containing an average of at least two silicon-bonded hydrogen atoms per molecule, and C. an amount of a microencapsulated hydrosilylation catalyst sufficient to promote curing of said composition at temperatures above 100° C. or in the presence of ultraviolet radiation having a wavelength in the range from 200 to 260 nanometers. where the concentration of said curing agent is sufficient to cure said composition, the sum of the average number of ethylenically unsaturated hydrocarbon radicals per molecule of polyorganosiloxane (A) and the average number of silicon-bonded hydrogen atoms in each molecule of said curing agent (B) is greater than 4, said catalyst is microencapsulated within a matrix or layer of at least one crosslinked organosiloxane compound. The non-crosslinked organosiloxane compound component used to make the crosslinked organosiloxane comprises at least two units of the formula $$R^2(CH=CH)_n—CH=CR^3C(O)OCH_2CH= CH—SiR^1_aO_{(3-a/2)} \quad (1)$$

where each $R^1$ is individually selected from the group consisting of unsubstituted and substituted monovalent hydrocarbon radicals, $R^2$ represents an aryl, alkoxyaryl or alkaryl radical, $R^3$ is —C≡N or —C(O)OR$^4$ where $R^4$ is hydrogen or an unsubstituted monovalent hydrocarbon radical, a is 0, 1 or 2 and n is 0 or a positive integer, with the proviso that n can be 0 only when $R^2$ represents a naphthyl radical, and said organosiloxane compound has been crosslinked by exposure to ultraviolet radiation in the wavelength range of from 300 to 400 nm.

A characteristic feature of curable organosiloxane compositions containing the microencapsulated hydrosilylation catalysts, also referred to herein as microcapsules, of this invention is their optical transparency. The transparency is believed due to the sub-micron diameter of at least a major portion, typically at least 50 percent, of the microcapsules and the low concentration of microcapsules required to achieved a rapid cure rate at elevated temperatures. Substantially none of the present microcapsules are larger than about 3 microns in diameter.

The present invention also provides a method for preparing the microencapsulated hydrosilylation catalysts. This method comprises the following sequence of steps:

1) exposing a solution consisting essentially of at least one photocrosslinkable organosiloxane compound, a solubilized platinum containing hydrosilylation catalyst and a volatile solvent to ultraviolet radiation within the wavelength range of from 300 to 400 nanometers for a sufficient time to crosslink said compound and evaporate substantially all of said solvent, and 2) isolating said microencapsulated catalyst, where the repeating units of said organosiloxane compound exhibit the formula

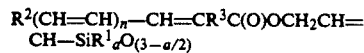

where each $R^1$ is individually selected from the group consisting of unsubstituted and substituted monovalent hydrocarbon radicals, $R^2$ represents an aryl, alkoxyaryl or alkaryl radical, $R^3$ is —C≡N or —C(O)OR$^4$ where $R^4$ is hydrogen or an unsubstituted monovalent hydrocarbon radical, a is 0, 1 or 2 and n is or a positive integer, with the proviso that n can be 0 only when $R^2$ represents a naphthyl radical.

The hydrosilylation catalyst is effectively isolated from the other ingredients of the curable organosiloxane composition until the composition is either heated to the melting or softening point of the crosslinked organosiloxane compound that encapsulates the hydrosilylation catalyst or the crosslinked organosiloxane compound is converted to an uncrosslinked material by exposing the curable composition to ultraviolet radiation in the range from 200 to 260 nanometers (nm), referred to as the "far" or "deep" ultraviolet range.

The ability of organosiloxane compounds derived from esters of alpha-cyano-beta-styrylacrylic acid to undergo a reversible photoinitiated crosslinking reaction is reported by R. Mercier et al. in the European Polymer Journal, 24, 7 (639-645 (1988).

The novelty of the present catalyst compositions resides in the crosslinked organosiloxane compound or compounds that encapsulate the hydrosilylation catalyst. The compounds are the product of a photointiated crosslinking involving organosiloxane compounds prepared by reacting an organohydrogenpolysiloxane or organohydrogendisiloxane with the propargyl radical of a propargyl ester of a carboxylic acid containing a sequence of at least two conjugated ethylenic double bonds between the carboxyl group of the ester and a terminal aryl, alkoxyaryl or alkaryl radical on the acid portion of the ester. When $R^3$ of formula 1 represents a naphthyl radical the sequence of conjugated double bonds can be replaced by a single ethylenic double bond.

The organosiloxane compounds represented by formula 1 are considered novel and are claimed in a copending patent application filed concurrently with the present specification.

The photo-initiated crosslinking of polyorganosiloxanes obtained by reacting an organohydrogensiloxane with the reaction product of a vinylchlorosilane and an alkali metal salt of cinnamic, beta-(2-furyl) acrylic or alpha-cyano-beta-styryl acrylic also referred to as 2-cyano-5-phenyl-2-4-pentadienecarboxylic) acids is described by R. Mercier, X. Coqueret and coworkers in the European Polymer Journal, vol. 24, No. 7, pages 639-645 (1988). The polyorganosiloxanes are characterized by the group

where the group

is derived from the initial organohydrogensiloxane reactant.

The organosiloxane compounds used to prepare the encapsulating materials for the present microencapsulated hydrosilylation catalysts differ from the polyorganosiloxanes described by Mercier and coworkers in the presence of the group

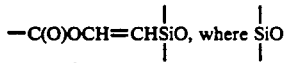

is a residue of the organohydrogensiloxane that is reacted with a propargyl ester represented by formula 2.

$$R^2(CH=CH)_n-CH=CR^3C(O)OCH_2CH=CH \quad (2)$$

The advantage of using this propargyl ester in place of the alkali metal acid salts of Mercier et al. is the unexpected selectivity of an organohydrogensiloxane reactant for the propargyl group in preference to the conjugation series of carbon double bonds in the acid portion of the ester.

The present organosiloxane compounds undergo the same type of reversible photoinitiated crosslinking reaction described in the aforementioned article by Mercier and coworkers. The present inventors discovered that this reaction can be utilized to microencapsulate liquid and solubilized hydrosilylation catalysts. These catalysts typically contain a metal from the platinum group of the periodic table, which includes platinum, palladium and rhodium. The catalyst ca be released by exposing the microencapsulated catalyst to ultraviolet radiation in the wavelength range of from 200 to 260 nm or by heating the microencapsulated catalyst to temperatures above about 120° C.

The photoinitiated cross-linking reaction of the present organosiloxane compounds is believed to involve formation of cyclobutane rings by pairs of ethylenically unsaturated carbon atoms on adjacent molecules of the organosiloxane. This reaction can be depicted as

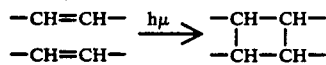

A major portion (at least ~80%) of the intermolecular bonds formed during this reaction can be broken by exposing the reaction product to ultraviolet radiation in the range from 200 to 260 nm, thereby at least partially converting the intermolecularly bonded compound to the original organosiloxane units represented by formula 1.

The microencapsulated hydrosilylation catalysts of the present invention can be prepared by irradiating a mixture of the catalyst in liquid or solubilized form and an organosiloxane compound containing units represented by formula 1 with ultraviolet radiation in the wavelength range from 300 to 400 nanometers (nm). This wavelength range is also referred to as the "near UV range". A wavelength of about 360 nanometers is preferred, based on the availability of UV sources and filters exhibiting emission in this wavelength region.

The amount of solvent used should be the minimum required to dissolve the hydrosilylation catalyst and the organosiloxane compound. An excess of solvent has been shown to decrease the rate of crosslinking of the organosiloxane compound in the presence of ultraviolet radiation.

The duration of the exposure required to achieve crosslinking of the organosiloxane compound and encapsulation of the hydrosilylation catalyst is a function of a number of variables, including but not limited to the intensity of the UV radiation reaching the organosiloxane compound and the energy threshold of the crosslinking reaction.

Preparation of the Photopolymerizable Organosiloxane Compound

The present organosiloxane compounds are prepared by reacting an organohydrogensiloxane with a propargyl ester of a carboxylic acid containing a sequence of conjugated carbon-to-carbon double bonds. The propargyl ester exhibits the formula $$R^2(CH=CH)_n-CH=CR^3C(O)OCH_2C=CH \quad (2)$$

In this formula $R^2$ represents an aryl, alkoxyaryl or alkaryl radical, $R^3$ is $-C\equiv N$ or $-C(O)OR^4$ where $R^4$ is hydrogen or an unsubstituted monovalent hydrocarbon radical, and n is 0 or a positive integer, with the proviso that n can be 0 only when $R^2$ represents a naphthyl radical.

Preparation of the Propargyl Ester (Formula 2)

A preferred class of the propargyl esters represented by formula 2 can be prepared using the Knoevenagel reaction, a base-catalyzed condensation between an aldehyde and the ester of an acid containing a labile hydrogen atom in the alpha position relative to the carbonyl group. This reaction is typically catalyzed by a base, and can be illustrated by the general equation $$R'CHO + R''CH_2COOR''' \rightarrow R'CH=C(R'')COOR'''$$

where R', R" and R'" represent monovalent hydrocarbon radicals.

The reaction used to prepare the propargyl ester of formula 2 can be represented by the equation

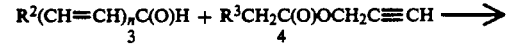
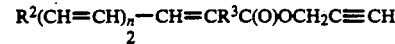

The reactants used to prepare this propargyl ester are the propargyl ester of a carboxylic acid containing a labile hydrogen atom on the alpha carbon relative to the carbonyl group (formula 4), referred to hereinafter as the propargyl ester reactant, and an aldehyde containing a terminal aromatic hydrocarbon radical represented by $R^2$ (formula 3). The number of ethylenic double bonds in the aldehyde is represented by n, the value of which is preferably 0 or 1, with the proviso that $R^3$ must represent naphthyl when n is 0.

The Ethylenically Unsaturated Aldehyde Reactant (Formula 3)

The ethylenically unsaturated aldehyde used in the Knoevenagel reaction can be represented by formula 3

$$R^2(CH=CH)_nC(O)H \quad (3)$$

where $R^2$ represents an aryl radical such as phenyl or naphthyl, an alkoxyaryl radical or an alkaryl radical, and the value of n is 0 or a positive integer, with the proviso that n can be 0 only when $R^2$ represents a naphthyl radical.

Suitable aldehydes represented by formula 3 contain an aromatic hydrocarbon radical at the terminal position and include but are not limited to cinnamaldehyde and products of an aldol condensation reaction between cinnamaldehyde, o- or p-methoxy cinnamaldehyde, benzaldehyde, naphthaldehyde or other aldehyde containing an aromatic hydrocarbon radical at the terminal position and an ethylenically unsaturated aliphatic aldehyde such as crotonaldehyde or acrolein.

When the carbonyl group of one of the aldehydes is bonded to an aromatic hydrocarbon ring structure or separated from the ring structure by a —CH=CH— group as in cinnamaldehyde, typically only one condensation product is formed.

The ethylenically unsaturated carbon atoms of the unsaturated aliphatic aldehyde 6 are adjacent to the aldehyde group [—C(O)H]. If both aldehydes (5 and 6) used in the aldol condensation contain ethylenically unsaturated carbon atoms in this position, this will maximize the number of conjugated double bonds present in the reaction product.

The aldol condensation reaction between cinnamaldehyde (5a) and crotonaldehyde (6a) can be represented by the following equation, where Ph represents a phenyl radical.

Ph—CH=CH—C(O)H + H₃C—CH=CH—C(O)H ⟶
    5a                      6a

Ph—CH=CH—CH=CH—CH=CH—C(O)H
3a

If desired it should be possible to repeat the condensation reaction to increase the number of sequential conjugated double bonds in the ethylenically unsaturated aldehyde that is subsequently reacted with the ester reactant represented by formula 5 to prepare the propargyl esters of the present invention represented by formula 2.

The Propargyl Ester Reactant (Formula 4)

The propargyl ester reactant used in the Knoevenagel reaction contains a labile hydrogen atom on the carbon atom adjacent to the carboxyl group and can be represented by formula 4.

$$R^3H_2CC(O)OC\equiv CH \quad (4)$$

where $R^3$ is as previously defined. $R^3$ preferably represents a cyano radical, this preference being based on the availability of alpha-cyanoacetic acid.

The Knoevenagel condensation reaction between the propargyl ester reactant (4) and the aromatic aldehyde (3) to form the propargyl ester represented by formula 2 is typically conducted at ambient temperature or below in the presence of a catalytic amount of an amine.

Suitable amine catalysts include but are not limited to aliphatic amines, aromatic amines such as aniline and p-nitroaniline. Heterocyclic amines such as piperidine are preferred.

The condensation reaction is typically carried out with the reactants dissolved in a common solvent, particularly when the reaction product is a solid. Useful solvents include but are not limited to cyclic ethers such as tetrahydrofuran and dioxane. The present inventors discovered that mixtures of cinnamaldehyde and naphthaldehyde containing from about 30 to about 50 weight percent of naphthaldehyde are preferred for use in preparing the organosiloxanes represented by formula 1, based on the long shelf life and rapid cure exhibited by organosiloxane compositions containing hydrosilylation catalysts encapsulated in the crosslinked mixture of siloxanes prepared using this combination of aldehydes.

Preparation of the Organosiloxane Compound, a Silylated Propargyl Ester (Formula 1)

The organosiloxane compounds that are photopolymerized in the presence of a hydrosilylation catalyst to prepare the microencapsulated catalysts of this invention can be prepared by the reaction of an organohydrogensiloxane with the propargyl group of the ester prepared as described in the preceding section of this specification and represented by formula 2.

$$R^3(CH=CH)_n-CH=CR^2C(O)OCH_2C\equiv CH \quad (2)$$

The reaction between silicon-bonded hydrogen atoms and a carbon-carbon double bond or triple bond is referred to as a hydrosilylation reaction and is typically catalyzed by a metal from the platinum group of the periodic table or a compound of such a metal. In addition to platinum the platinum group of metals includes rhodium and palladium. To provide the desired selectivity of reaction at the actylenic carbon atoms of the propargyl ester it is preferred to use platinum or a compound of this metal.

Chloroplatinic acid, and more particularly complexes of chloroplatinic acid with liquid ethylenically unsaturated organosilicon compounds such as sym-tetramethyldivinyldisiloxane, are preferred catalysts for the reaction of the propargyl ester with the organosilicon compound containing silicon-bonded hydrogen atoms. This preference is based on the selectivity of these catalysts in limiting the site of the hydrosilylation reaction to the propargyl group of the ester represented by formula 3 and the high yield of the desired organosilicon compound.

The propargyl ester represented by formula 2 and the organohydrogensiloxane are preferably used in substantially equimolar amounts to avoid undesirable side reactions between the silicon bonded hydrogen atoms and the conjugated carbon-carbon double bonds present in the acid portion of the propargyl ester.

The hydrosilylation reaction involving the propargyl ester is generally carried out in the presence of a solvent that will not participate in this reaction. Preferred solvents include but are not limited to liquid aromatic and saturated aliphatic hydrocarbons.

While the hydrosilylation reaction will proceed at room temperature, the reaction mixture is preferably heated at between 70° and 110° C. to increase the rate of the reaction. The preferred temperature will depend upon a number of variables, including the type of organohydrogensilane or organohydrogensiloxane used. The course of the reaction can conveniently be followed using infrared spectroscopy to observe the decreasing concentration of the propargyl (—H$_2$C—C≡CH) and SiH groups as the reaction proceeds.

Preferred organohydrogensiloxanes include but are not limited to symmetrical tetraalkyldihydrogendisiloxanes, resinous organosiloxane copolymers containing phenylsilsesquioxane (PhSiO$_{3/2}$) and dimethylhydrogensiloxy units, and substantially linear organopolysiloxanes wherein at least a portion of the repeating units are represented by the formula R$^1$HSiO, where R$^1$ represents an unsubstituted or substituted monovalent hydrocarbon radical as defined in the preceding specification, any remaining non-terminal units are R$^1_2$SiO, and the terminal units are triorganosiloxy or diorganohydrogensiloxy, where the organic groups are hydrocarbon radicals selected from the same group as R$^1$. Alternatively, the silicon-bonded hydrogen atoms can be present only at the terminal positions of the organopolysiloxane molecule.

The organosiloxanes obtained as products of the hydrosilylation reaction are typically solids at room temperature and can be purified using conventional recrystallization techniques.

The Hydrosilylation Catalyst

Platinum-containing hydrosilylation catalysts suitable for preparing the microencapsulated catalysts of this invention include reaction products of chloroplatinic acid with an ethylenically unsaturated organosilicon compound such as sym-divinyltetramethyldisiloxane. These reaction products are described by Willing in U.S. Pat. No. 3,419,593 and incorporated herein by reference. Other platinum-containing hydrosilylation catalysts considered useful for preparing the present microencapsulated catalysts include those described in U.S. Pat. Nos. 3,159,601; 3,159,602; 3,220,972; 3,296,291; 3,516,946; 3,814,730; and 3,928,629, all of which are incorporated herein by reference as disclosures of platinum-containing hydrosilylation catalysts.

Platinum-containing hydrosilylation catalysts form coordination complexes with ethylenically or acetylenically unsaturated silicon or organic compounds. These compounds include organosilicon compounds such as the tetramethyldivinyldisiloxane, present as the coordinating agent in preferred platinum-containing hydrosilylation catalysts, and many of the inhibitors used to retard the activity of the catalyst at temperatures below about 50 degrees C.

Ethylenically or acetylenically unsaturated organic compounds containing one or more polar groups such as carbonyl or hydroxyl are particularly preferred coordinating agents for platinum-containing hydrosilylation catalysts.

A particularly preferred class of hydrosilylation catalysts that are microencapsulated by organosiloxane compounds represented by formula 1 include coordination complexes of platinum. Coordinated platinum compounds are most preferably derived from halide compounds of platinum group metals such as chloroplatinic acid. The chloroplatinic acid can be initially present as the commercially available hexahydrate or in the anhydrous form disclosed by Speier in U.S. Pat. No. 2,823,218.

Polymerization of the Organosiloxane Compound of Formula 1 and Preparation of Microencapsulated Hydrosilylation Catalysts The microencapsulated hydrosilylation catalysts of this invention are formed by exposing homogeneous solutions consisting essentially of (a) at least one of the organosiloxane compounds containing repeating units represented by formula 1 (b) a hydrosilylation catalyst and (c) a suitable volatile solvent for (a) and (b) to ultraviolet (UV) light exhibiting a wavelength of from 300 to 400 nm. for a period of time sufficient to form microcapsules of crosslinked containing the hydrosilylation catalyst. Suitable solvents exhibit a substantial vapor pressure under ambient conditions to facilitate their removal during the photoinitiated crosslinking reaction, and include but are not limited to ketones such as acetone containing a total of from 3 to 5 carbon atoms and liquid chlorinated hydrocarbons such as methylene chloride.

In accordance with a preferred method for preparing the microencapsulated hydrosilylation catalyst, the solution containing at least one of the organosiloxane compounds of formula 1 and the hydrosilylation catalyst is placed in a tray or other suitable container to form a layer of from about 2 to about 5 mm in depth. The layer of liquid is then exposed to the radiation from a suitable lamp or other ultraviolet source exhibiting an emission maximum in the range from 300 to 400 nm, preferably about 360 nm. The exposure time required to form a crosslinked organosiloxane compound is dependent upon a number of variables, including the intensity of the radiation at the surface of the liquid layer and the thickness of the layer. For intensities in the range from about 5 to about 15 milliwatts per cm$^2$ and a layer thickness of about 4 mm the exposure time is typically from one to about three hours. Substantially all of the solvent used to dissolve the organosiloxane compound and the hydrosilylation catalyst evaporates during this exposure period. It is therefore desirable to use means for removing the volatilized solvent from the exposure area.

For some applications it may be desirable to use mixtures of two or more organosiloxane compounds to prepare the microencapsulated hydrosilylation catalyst. A particularly preferred combination contains from 50 to 95 percent, based on the weight of said combination, of a first organosiloxane compound containing repeating units of formula 1 where R$^2$ is phenyl and n is 1. In the second organosiloxane compound R$^2$ is naphthyl and n is 0. In both compounds R$^3$ is the cyano group, R$^1$ is methyl, a is 2 and the organosiloxane compound is a disiloxane.

The product of the UV initiated polymerization is typically a solid consisting essentially of microcapsules wherein the hydrosilylation catalyst is completely enveloped within a layer or matrix of the crosslinked organosiloxane compound.

The average diameter of microcapsules prepared using the method of this invention is less than three microns. Preferably the diameter of at least a portion of the microcapsules is less than one micron.

To avoid premature rupturing of the microcapsules during storage the curing catalyst should not have a significant vapor pressure at temperatures from 25 to about 60 degrees C.

For the present microencapsulated hydrosilylation catalysts, also referred to as microcapsules, to function effectively in a curable organosiloxane composition the crosslinked organosiloxane compound that encapsulates the catalyst must melt or soften sufficiently to release the catalyst at or slightly below the desired curing temperature of the organosiloxane composition.

The present microcapsules are essentially spherical in contour with diameters of up to about 3 microns. Diameters of less than 3 microns are preferred to ensure that curable compositions containing these microcapsules will be optically transparent.

The present inventors found it difficult to encapsulate all of the hydrosilylation catalyst in a microcapsule containing one layer of crosslinked organosiloxane material when the hydrosilylation catalyst exceeds about 5 percent of the combined weight of the catalyst and the crosslinked organosiloxane compound present as the shell portion of the microcapsules. The catalyst preferably constitutes from about 2 to about 2.5 weight percent of the microcapsules.

Curable Organosiloxane Compositions Containing the present Microencapsulated Catalyst In addition to the microencapsulated curing catalyst described in the preceding sections of this specification the curable organosiloxane compositions of this invention typically comprise a polyorganosiloxane, referred to hereinafter as ingredient A, containing an average of at least two ethylenically unsaturated hydrocarbon radicals per molecule.

Ingredient A can be any polyorganosiloxane curable by a platinum-catalyzed hydrosilylation reaction. The viscosity of ingredient A can range from a liquid to a high viscosity gum that will flow only under pressure. Two of the ethylenically unsaturated hydrocarbon radicals presened in ingredient A are located at the terminal positions of the molecule in the form of dimethylvinylsiloxy, methylphenylvinylsiloxy or dimethyl-1-hexenyl groups.

If the curable composition is a liquid or pasty material, the viscosity of ingredient A is preferably from 1 to 500 Pa.s. Polymers of this type are well known and commercially available. In addition to diorganosiloxane and terminal triorganosiloxy groups ingredient A can contain one or more monoorganosiloxane units per molecule, resulting in branching of the polymer molecule. Polymers of this type are described in U.S. Pat. No. 3,284,406 to Nelson, which issued on Nov. 8, 1966.

Alternatively, ingredient A can be a semi-solid polydiorganosiloxane, known in the art as a gum, exhibiting a viscosity of up to 1000 Pa.s or greater at 25 degrees C. Curable compositions containing this type of polydiorganosiloxane are typically prepared by blending the ingredients under high shear using a two- or three roll rubber mill or dough-type mixer.

Surprisingly it has been found that the microencapsulated hydrosilylation catalysts of this invention do not rupture or collapse under the conditions used to process these high consistency organosiloxane compositions. The catalysts can therefore be incorporated this type of curable composition using conventional blending methods.

Ingredient A is cured by a hydrosilylation reaction between the ethylenically unsaturated hydrocarbon radicals of this ingredient and silicon-bonded hydrogen atoms of an organohydrogensiloxane, ingredient B. In a typical curable composition of this invention one or more polydiorganosiloxanes containing an average of at least two ethylenically unsaturated hydrocarbon radicals per molecule react with a relatively low molecular weight, liquid organohydrogensiloxane containing an average of at least three silicon bonded hydrogen atoms per molecule.

The silicon-bonded hydrocarbon or substituted hydrocarbon radicals that constitute the organic groups bonded to the silicon atoms of ingredients A and B are monovalent unsubstituted or substituted hydrocarbon radicals containing from 1 up to 20 or more carbon atoms. Halogen atoms are preferred substituents. Preferably these hydrocarbon radicals are lower alkyl, phenyl or a perfluoroalkylethyl radical such as 3,3,3-trifluoropropyl, this preference being based on the availability of the intermediates used to prepare ingredient A and B. Most preferably at least a portion of the repeating units of ingredients A and B contain silicon bonded methyl radicals, and Ingredient B can contain from as few as four silicon atoms per molecule up to an average of 20 or more, and preferably exhibits a viscosity of up to 10 Pa.s at 25 degrees C. Ingredient B contains repeating units of the formulae $HSiO_{1.5}$, RHSiO and/or $R^2HSiO_{0.5}$. The molecules of this ingredient may also include one or more monoorganosiloxane, diorganosiloxane, triorganosiloxy and $SiO_{4/2}$ units that do not contain silicon bonded hydrogen atoms. In these formulae R is a monovalent hydrocarbon radical as defined in the preceding section of this specification.

Alternatively, ingredient B can be a cyclic compound containing at least 4 organohydrogensiloxane units of the formula RHSiO or a compound of the formula $HR_2SiO(HRSiO)_aSiR_2H$, where a is at least 1.

Most preferably R is methyl and ingredient B is a linear trimethylsiloxy terminated polymethylhydrogensiloxane or a dimethylsiloxane/methylhydrogensiloxane copolymer containing an average of from 5 to about 50 repeating units per molecule of which from 30 to 100 percent are methylhydrogensiloxane units.

The molecular weights of ingredients A and B together with the number and distribution of the silicon-bonded hydrogen atoms and ethylenically unsaturated hydrocarbon radicals within these ingredients will determine the location of crosslinks in the cured product, which can range from a glass-like resin to an elastomer to a gel.

The concentration of crosslinks per unit volume is often referred to as the "crosslink density" and determines certain physical properties of the cured elastomer, particularly hardness, tensile strength and elongation. The particular combinations of polydiorganosiloxane(s) and curing agent(s) yielding the desired combination of physical properties can readily be determined by routine experimentation with a knowledge of this invention.

The molar ratio of silicon bonded hydrogen atoms in the organohydrogensiloxane to the vinyl or other ethylenically unsaturated hydrocarbon radicals present in ingredient A is a major factor in determining the properties of the elastomer or other cured material obtained from the composition. Because of the difficulty often experienced in achieving a complete reaction between all of the silicon bonded hydrogen atoms and all of the vinyl or other ethylenically unsaturated hydrocarbon radicals present in the reaction mixture, it is desirable to have an stoichiometric excess of one of these species in a curable composition. A ratio of from 1.0 to 1.6 silicon bonded hydrogen atoms per vinyl or other ethylenically unsaturated hydrocarbon radical has been found to yield optimum combinations of physical properties. The preferred ratio for a given composition will be determined at least in part by the average molecular weight of ingredient A and the type of curing agent.

The consistency of the present compositions can vary from a flowable liquid to a semi-solid paste to a high consistency gum that will flow only under high shear. In addition to the aforementioned ingredients the compositions can contain other additives including but not limited to reinforcing and non-reinforcing fillers, treating agents for these fillers, pigments, processing aids, stabilizers and flame retardants. It should be understood that some of these additives will detract from the optical transparency of the curable and cured organosiloxane compositions containing the preferred platinum-containing hydrosilylation catalysts.

The amount of microencapsulated curing catalyst present in the curable compositions of this invention is typically not restricted so long as there is a sufficient amount to promote the reaction between ingredients A and B. Because of the small particle size of the present microencapsulated catalysts it is possible to use catalyst concentrations equivalent to as little as 1 part by weight or less, based on platinum-group metal, per million parts of curable composition and still obtain a uniformly cured product.

For some applications it may be desirable to add one of the known platinum catalyst inhibitors to the present curable organosiloxane compositions to alter the cure profile of the composition. It has been found that the presence of from about 100 to about 500 parts per million, based on the weight of the curable composition, of an alkynol type of platinum catalyst inhibitor will lengthen the induction period prior to the initiation of the curing reaction, measured using a torque rheometer, while decreasing the time interval required to complete curing of the composition.

EXAMPLES

The following examples describe preferred embodiments of the present microencapsulated curing catalysts methods for preparing these catalysts and one-part, storage stable curable organosiloxane compositions containing the microencapsulated curing catalysts. The examples should not be interpreted as limiting the scope of the invention defined in the accompanying claims. Unless otherwise specified all parts and percentages are by weight and all viscosities were measured at 25 degrees C. In the formulae Me represents the methyl radical and Ph represent the phenyl radical.

Preparation of Propargyl Cyanoacetate 1.6 parts of propargyl alcohol and 1 part of cyanoacetic acid were dissolved in 4.7 parts of chloroform. 0.2 parts of a 98 percent by weight solution of aqueous sulfuric acid were added as a catalyst and the resultant mixture was heated for 5.5 hours at a temperature of 61° C. The crude ester was washed with water. Volatile materials were removed using reduced pressure. The ester, represented the formula N≡CCH₂C(O)OCH₂C≡CH, was isolated in 71 percent yield.

EXAMPLE 2

Reaction of Propargyl Cyanoacetate with (a) Cinnamaldehyde to form Propargyl 2-cyano-5-phenyl-2,4-pentanedienoate (PCPPD, formula 2a) and with (b) Naphthaldehyde A Knoevenagel condensation was conducted by dissolving 15.5 g (0.126 mol) of propargyl cyanoacetate in 40 cc of dioxane in an open flask with stirring. An equimolar amount (16.6 g) of cinnamaldehyde was then added to the reaction mixture and the flask cooled in an ice-water mixture. 0.4 cc of piperidine were then gradually over a period of about 10 minutes as a reaction catalyst. A yellow solid precipitated in about 5 minutes. The mixture was stirred briefly, then allowed to remain under ambient conditions for 3.5 hours, at which time the solid was isolated by filtration and washed with water. A 91% yield of crude product melting at 133° C. was obtained. This material was recrystallized from toluene to yield a product melting at 138° C.

The infra-red and proton nuclear magnetic resonance spectra of the recrystallized compound exhibited maxima characteristic of the C≡CH, C≡N, C≡C, C=O, —COO, CH₂C≡C and C=C—C=C groups, and was consistent with the expected product, PCPPD, corresponding to formula 2a

PhCH=CHCH=C(CN)C(O)OCH₂C≡CH

The corresponding condensation product using naphthaldehyde was prepared by replacing the cinnamaldehyde with an equimolar quantity of naphthaldehyde. This product melted at 116° C. and will be referred to as 2b. The formula for this product is the same as 2a, with the exception that Ph is replaced with the 1-naphthyl radical.

EXAMPLE 3

Hydrosilylation of PCPPD and the Corresponding Naphthaldehyde Derivative with 1,1,3,3-Tetramethyldisiloxane (TMDS)

A 16.7 percent solution of PCPPD in heated toluene was combined with an amount of a platinum hydrosilylation catalyst equivalent to 0.004 weight percent platinum, based on the weight of toluene. The catalyst was a reaction product of hexachloroplatinic acid and sym-tetramethyldivinyldisiloxane that has been diluted with a liquid dimethylvinylsiloxy terminated polydimethylsiloxane in an amount sufficient to achieve a platinum content of 4.2 weight percent. The resultant solution was heated to a temperature of between 70° and 75° C. at which time an amount of 1,1,3,3-tetramethyldisiloxane (TMDS) equivalent to a molar ratio of silicon-bonded hydrogen atoms to C≡C radicals in the PCPPD of 1:1 was added dropwise to the reaction mixture.

Heating of the resultant reaction mixture was continued for an additional four hours following completion of the TMDS addition, at which time the toluene was removed from the reaction mixture under reduced pressure to yield the desired PCPPD/TMDS reaction product as a yellow solid exhibiting a melting point of 78° C. The IR absorption spectrum of this product exhibited maxima characteristic of the C≡N, C=O, ≡Si—O—Si≡ and —CH=CH—CH=CH— groups, which is consistent with a compound corresponding to formula 1a.

[PhCH=CHCH=C(CN)C(O)OCH₂CH=CH=SiMe₂]₂O         (1a)

where Ph represents a phenyl radical and Me represents a methyl radical.

The naphthaldehyde derivative of the organosiloxane compound corresponding to formula 1a where PhCH=CH is replaced with the 1-naphthyl radical was prepared using the same procedure used to prepare organosiloxane compound 1a, but replacing propargyl ester 2a with an equimolar quantity of propargyl ester 2b.

Preparation of Microencapsulated Hydrosilylation Catalysts

A solution was prepared by dissolving (1) 1 part of organosiloxane compound 1a prepared as described in the preceding section of this example, 1 part of organosiloxane compound 1b, or a mixture containing 0.6 part of compound 1a and 0.4 part of compound 1b, (2) 0.6 part of a coordination complex of hexachloroplatinic acid and sym-tetramethyldivinyldisiloxane containing 4 weight percent of platinum metal in (3) 1 part of acetone.

Each of the resultant solutions was poured into a tray to form a 4 mm-thick layer of liquid. The surface of the liquid was located 2 inches (5 cm.) below a 360 nm ultraviolet source. The energy content of the radiation produced by the source was 15 mw/cm2. The exposure time was 2 hours, equivalent to a dosage of 108 joules/cm$^2$.

Examination of the resultant brownish-black waxy solid under a microscope revealed the solid to be composed of microcapsules exhibiting an average diameter of 0.2 micrometer.

EXAMPLE 4

Evaluation of the Microencapsulated Catalyst of Example 3

Two catalyst master batch was prepared by blending one part of one of the three encapsulated platinum catalysts prepared as described in Example 3 on a three-roll mill with nine parts of a mixture prepared by blending to homogeneity (1) 100 parts of a dimethylvinylsiloxy terminated polydimethylsiloxane having a viscosity of about 2.1 Pa.s at 25 degrees C., 2.9 parts of water, 9 mole percent of methylvinylsiloxane units and exhibiting a Williams plasticity of from 1.4 to 1.7 mm.

26 parts of a fume silica having a nominal surface area of 250 m$^2$ per gram, and 1 part of a hydroxyl-terminated dimethylsiloxane-/methylvinylsiloxane copolymer containing about 10 weight percent of vinyl radicals and about 16 weight percent of hydroxyl groups, and 5 parts of a hydroxyl-terminated polymethylphenylsiloxane having a viscosity of about 0.5 Pa.s at 25° C. and a hydroxyl content of about 4.5 weight percent.

A curable composition of this invention was prepared by blending 0.48 part or 0.24 part of each of the two catalyst master batches described in the preceding section of this example was into separate batches of the high consistency composition I to form a curable composition of the present invention. Some of the compositions were also blended with 300 ppm of 1-ethynyl-1-cyclohexanol (ETCH), a known platinum catalyst inhibitor, to determine the effect of this additive on the storage stability and cure profile of the composition.

The cure profiles of the compositions were measured using a torque rheometer at a temperature of 170° or 190° C. The elapsed time required for the torque to increase from the initial value and the elapsed time required for the torque to increase to 50 and 90 percent of the final value (Tmax) are recorded in Table 1 as t2, t50 and t90, respectively.

A second portion of each of each curable composition was stored at 40° C. and the plasticity of each composition was measured 2 weeks and 4 weeks after it had been prepared.

A third portion of each composition was cured for 10 minutes in a hydraulic press maintained at a temperature of 170° C. The samples were allowed to cool for 16 hours prior to measurement of their compression set.

The results of the storage stability and compression set determinations are recorded in Table 1.

TABLE 1

| Type | Parts* | Cure Temp. | Tmax kN/M | t2 Min | t50 Min | t90 Min | Comp Set | Initial | 2 wk | 4 wk | ETCH |
|---|---|---|---|---|---|---|---|---|---|---|---|
| Organosiloxane Compound | | | | | | | | Plasticity (mm) | | | |
| 1a | 0.48 | 170 | 11.2 | 1.6 | 3.9 | 12.2 | 38 | 0.23 | 0.27 | 0.32 | 0 |
| 1a | 0.48 | 190 | 12.3 | 1.2 | 3.0 | 9.8 | 27 | | | | |
| 1b | 0.48 | 170 | 14.4 | 0.6 | 2.0 | 5.0 | 24 | Cured in 4 wks. @25° C. | | | 0 |
| 1a/1b | 0.24 | 170 | 13.9 | 2.2 | 3.6 | 8.9 | 22 | 0.24 | 0.28 | 0.32 | 300 |
| 1a/1b | 0.24 | 190 | 14.3 | 1.2 | 2.1 | 5.4 | 16 | | 300 | | |
| 1a/1b | 0.24 | 170 | 11.3 | 1.5 | 4.0 | 12.5 | 28 | 0.24 | 0.27 | 0.29 | 0 |
| 1a/1b | 0.24 | 190 | 13.1 | 0.9 | 2.4 | 9.5 | 26 | | | | 0 |
| 1a/1b | 0.48 | 170 | 14.3 | 1.6 | 2.6 | 6.2 | 20 | 0.23 | 0.34 | 0.39 | 300 |
| 1a/1b | 0.48 | 190 | 13.8 | 1.2 | 2.2 | 5.5 | 15 | | 300 | | |

*parts of encapsulated catalyst by weight based on 201.71 parts of composition minus catalyst parts of hexamethyldisilazane, and 40 parts of a fume silica having a nominal surface area of 250 m$^2$ per gram.

A high consistency organosiloxane composition (I) was prepared by blending to homogeneity (1) 1.71 parts of a trimethylsiloxy- terminated polydiorganosiloxane having an average of five methylhydrogensiloxane units and three dimethylsiloxane units per molecule with a silicon-bonded hydrogen atom content in the range from about 0.7 to 0.8 weight percent, and (2) 200 parts of a high consistency organosiloxane composition that had been prepared by blending the following ingredients to homogeneity:

68 parts of a high consistency dimethylvinylsiloxy-terminated polydimethylsiloxane containing 0.142

That which is claimed is:

1. A one-part, storage stable, heat curable organosiloxane composition comprising
   A. a liquid or gum polyorganosiloxane containing an average of at east two ethylenically unsaturated hydrocarbon radicals per molecule;
   B. as a curing agent for said composition, an organohydrogensiloxane containing an average of at least two silicon-bonded hydrogen atoms per molecule, and
   C. an amount of a microencapsulated hydrosilylation catalyst sufficient to promote curing of said composition at temperatures above 100° C. or in the presence of ultraviolet radiation having a wavelength in the range from 200 to 260 nanometers, where the concentration of said curing agent is sufficient to cure said composition, the sum of the average number of ethylenically unsaturated hydrocarbon radicals per molecule of polyorganosiloxane (A) and the average number of silicon-bonded hydrogen atoms in each molecule of said curing agent (B) is greater than 4, said catalyst is microencapsulated within a matrix or layer of at least one crosslinked organosiloxane compound, the non-crosslinked organosiloxane compound component used to make the crosslinked organosiloxane, comprises at least two units of the formula

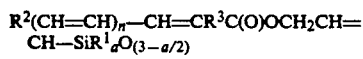

where each $R^1$ is individually selected from the group consisting of unsubstituted and substituted monovalent hydrocarbon radicals, $R^2$ represents an aryl, alkoxyaryl or alkaryl radical, $R^3$ is $-C\equiv N$ or $-C(O)OR^4$ where $R^4$ is hydrogen or an unsubstituted monovalent hydrocarbon radical, a is 0, 1 or 2 and n is 0 or a positive integer, with the proviso that n can be 0 only when $R^2$ represents a naphthyl radical, and said organosiloxane compound has been crosslinked by exposure to ultraviolet radiation in the wavelength range of from 300 to 400 nm.

2. A composition according to claim 1 where $R^1$ is selected from the group consisting of alkyl radicals containing from 1 to 10 carbon atoms, cycloalkyl, aryl, alkaryl, aralkyl and substituted alkyl radicals where the substituent is a halogen atom;

$R^2$ represents phenyl, o-, m-, or p-methoxyphenyl or naphthyl;

n is 0, 1, or 2;

said hydrosilylation catalyst constitutes up to 5 percent of the combined weight of said catalyst and said crosslinked organosiloxane compound;

the average particle diameter of the microencapsulated hydrosilylation catalyst is less than 3 micrometers;

the ethylenically unsaturated hydrocarbon radicals present in said polyorganosiloxane are vinyl or 5-hexenyl;

the remaining silicon bonded hydrocarbon radicals present in said polyorganosiloxane and said organohydrogensiloxane are selected from the group consisting of alkyl containing from 1 to 4 carbon atoms, phenyl, and 3,3,3-trifluoropropyl; and said hydrosilylation catalyst is a compound of a platinum-group metal.

3. A composition according to claim 2 where $R^1$ is methyl, phenyl, or 3,3,3-trifluoropropyl; $R^3$ is a cyano group; n is 0 and $R^2$ is naphthyl or n is 1 and $R^2$ is phenyl; a is 1 or 2; at least 50 percent of said microencapsulated catalyst exhibits a particle diameter below one micrometer; said hydrosilylation catalyst is a coordinated platinum compound prepared by reacting chloroplatinic acid with an ethylenically unsaturated organosilicon compound; said polyorganosiloxane is a gum exhibiting a viscosity greater than 1000 Pa.s at 25° C.; and the viscosity of said organohydrogensiloxane is up to 10 Pa.s at 25° C.

4. A composition according to claim 3 where said catalyst is microencapsulated within a layer consisting essentially of a first crosslinked organosiloxane compound wherein $R^1$ is methyl; $R^2$ is phenyl, $R^3$ is a cyano group, a is 2 and n is 1; and a second crosslinked organosiloxane compound wherein $R^1$ is methyl, $R^2$ is naphthyl; $R^3$ is a cyano group; a is 2; n is 0; and said first organosiloxane compound constitutes from 50 to 95 percent of the combined weight of said first and second organosiloxane compounds.

5. A composition according to claim 3 where said composition contains an amount of an platinum catalyst inhibitor sufficient to alter the curing profile of said composition.

6. A composition according to claim 5 where said inhibitor is an alkynol.

* * * * *